United States Patent [19]

Eichman et al.

[11] Patent Number: 5,399,089
[45] Date of Patent: Mar. 21, 1995

[54] ORAL HYGIENE APPLIANCE

[75] Inventors: Kim T. Eichman, Fort Collins; John E. Smith, Loveland; Clifford J. Snyder, Fort Collins, all of Colo.; Gerald T. Swanson, Norwood, Mass.

[73] Assignee: Teledyne Industries, Inc., Fort Collins, Colo.

[21] Appl. No.: 105,293

[22] Filed: Aug. 11, 1993

[51] Int. Cl.⁶ ................. A61C 17/02; A61H 9/00
[52] U.S. Cl. .................. 433/80; 601/162; 601/165
[58] Field of Search .............. 433/80, 84, 85, 88; 128/162, 163, 165; 222/318; D24/214

[56] References Cited

U.S. PATENT DOCUMENTS

| Re. 27,274 | 1/1972 | Mattingly . | |
|---|---|---|---|
| 3,578,884 | 5/1971 | Jacobson | 601/162 X |
| 4,337,040 | 6/1982 | Cammack et al. | 433/80 |
| 4,374,354 | 2/1983 | Petrovic et al. . | |
| 4,442,830 | 4/1984 | Markau | 433/80 X |
| 4,585,415 | 4/1986 | Hommann | 433/80 |
| 4,607,627 | 8/1986 | Leber et al. . | |
| 4,824,368 | 4/1989 | Hickman | 433/80 |
| 4,862,876 | 8/1988 | Lih-Sheng | 601/162 |
| 4,958,629 | 9/1990 | Peace et al. | 601/165 |
| 4,989,590 | 2/1991 | Baum et al. . | |
| 5,029,576 | 7/1991 | Evans, Sr. | 433/80 X |

*Primary Examiner*—Nicholas D. Lucchesi
*Attorney, Agent, or Firm*—Hugh H. Drake

[57] ABSTRACT

An oral hygiene appliance includes a base on which upstands a cabinet having top, front and rear vertical walls. A pair of recesses are formed in either side of that front wall. A plurality of seats within those recesses are each receptive of a jet tip. An inlet is defined in the top wall. A cover is shaped to envelope the cabinet over the recesses and the inlet with the cover being invertable to serve as a reservoir. Disposed within the cabinet is a pump responsive to a pressure control for delivering water received from the inlet.

Seated toward one end of the base is the lower end of an elongated electric toothbrush body. Individual brushes are seated in the base around the body and those brushes ordinarily to the rear of the body are elevated on a pedestal. At the opposite end of the base is a well in which is seated the lower end of a handle in which a faceted lower end of one of the jet tips may be captivated. A pressure control unit cooperates with the pump assembly to guard against excessive pressure and permit easy control of the level of pressure delivered from the jet tip mounted in the handle.

21 Claims, 12 Drawing Sheets

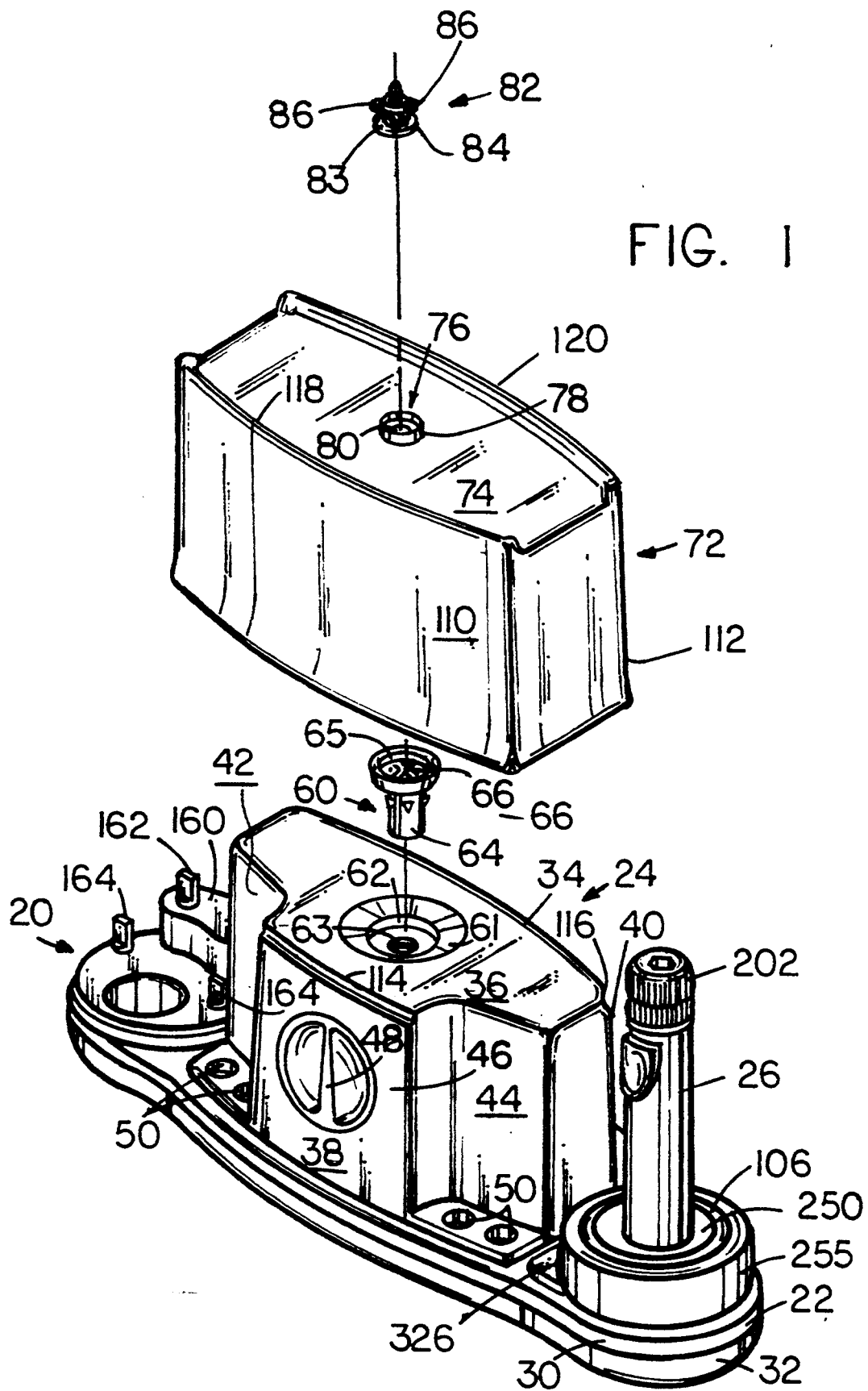

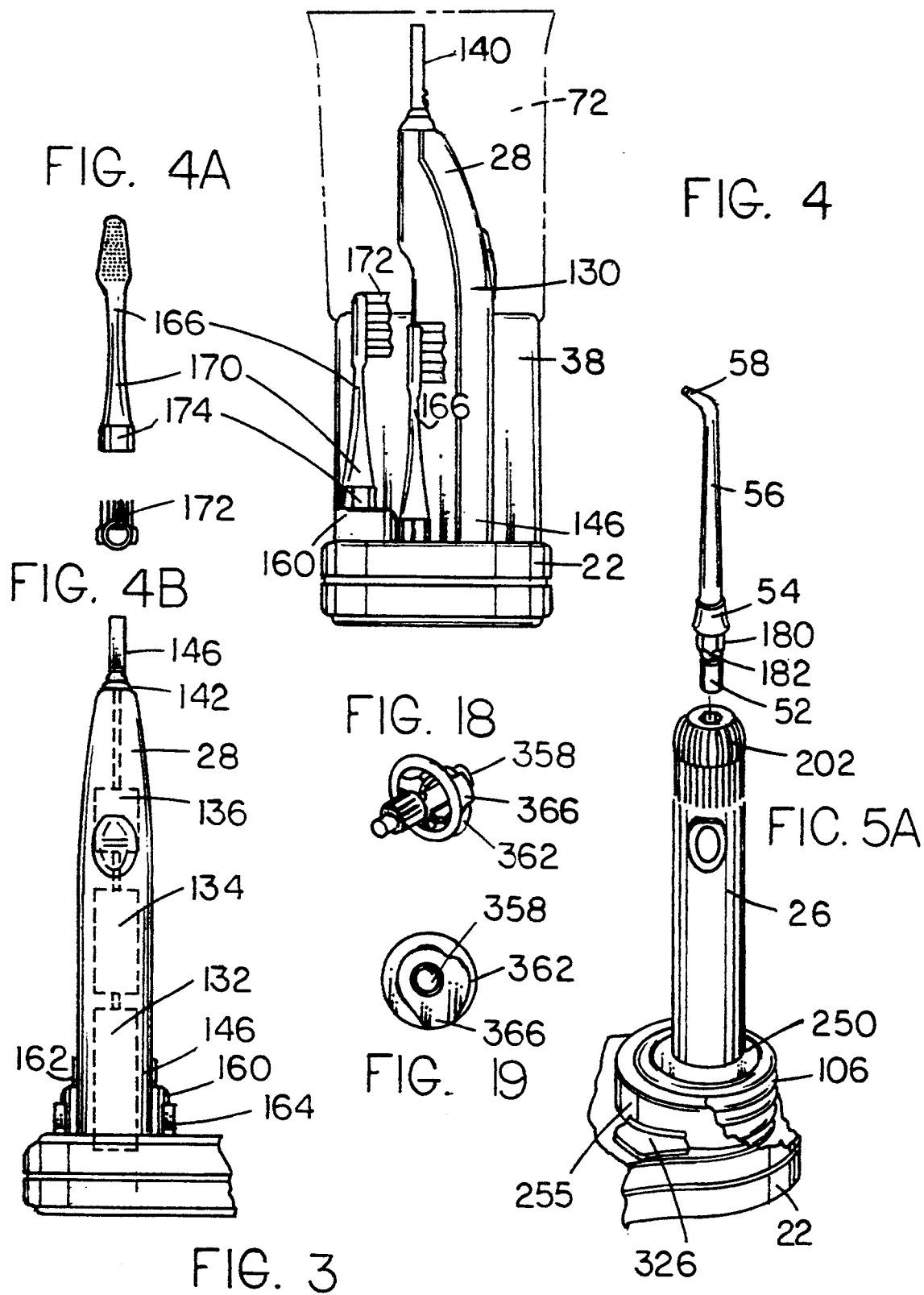

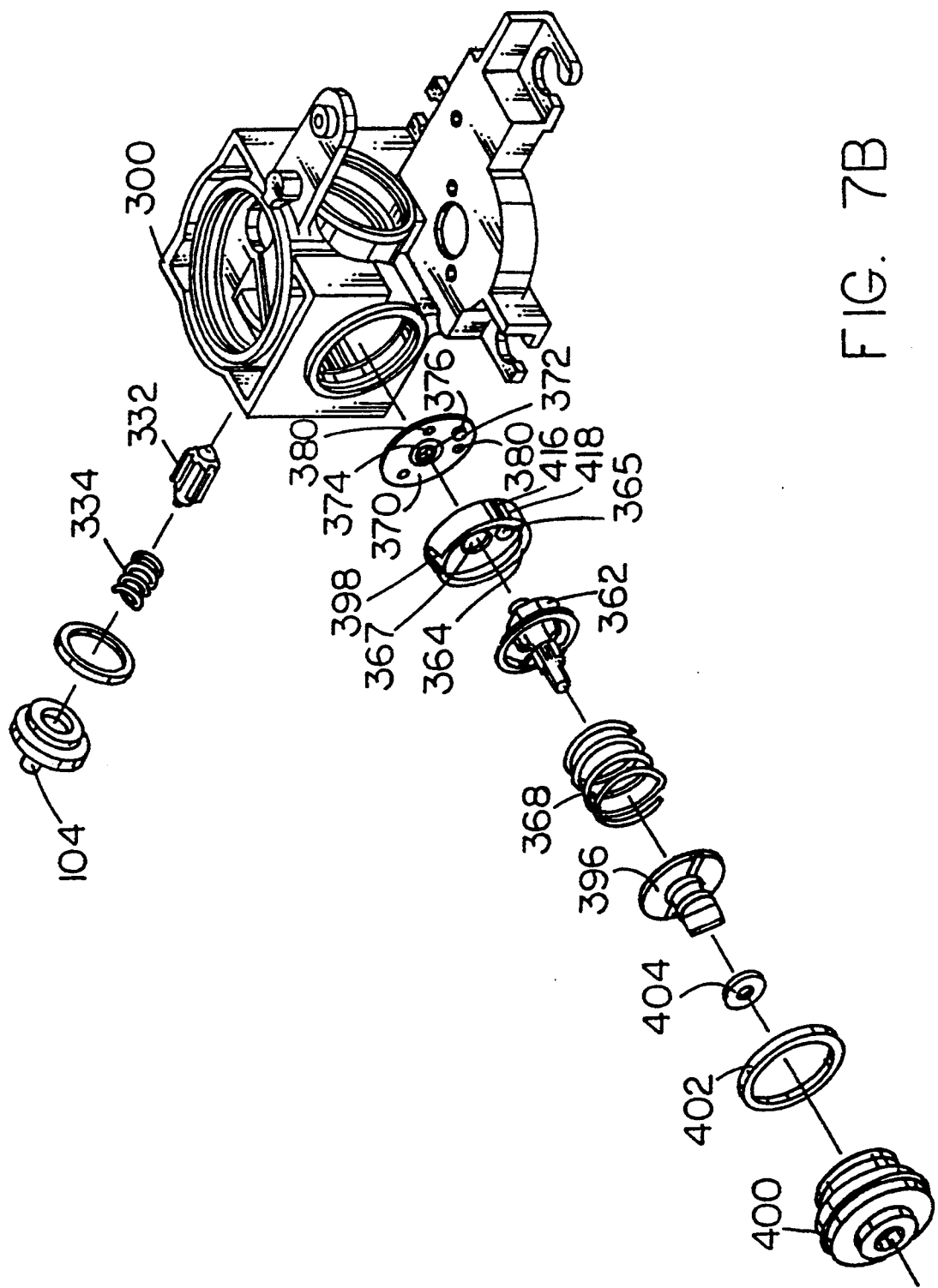

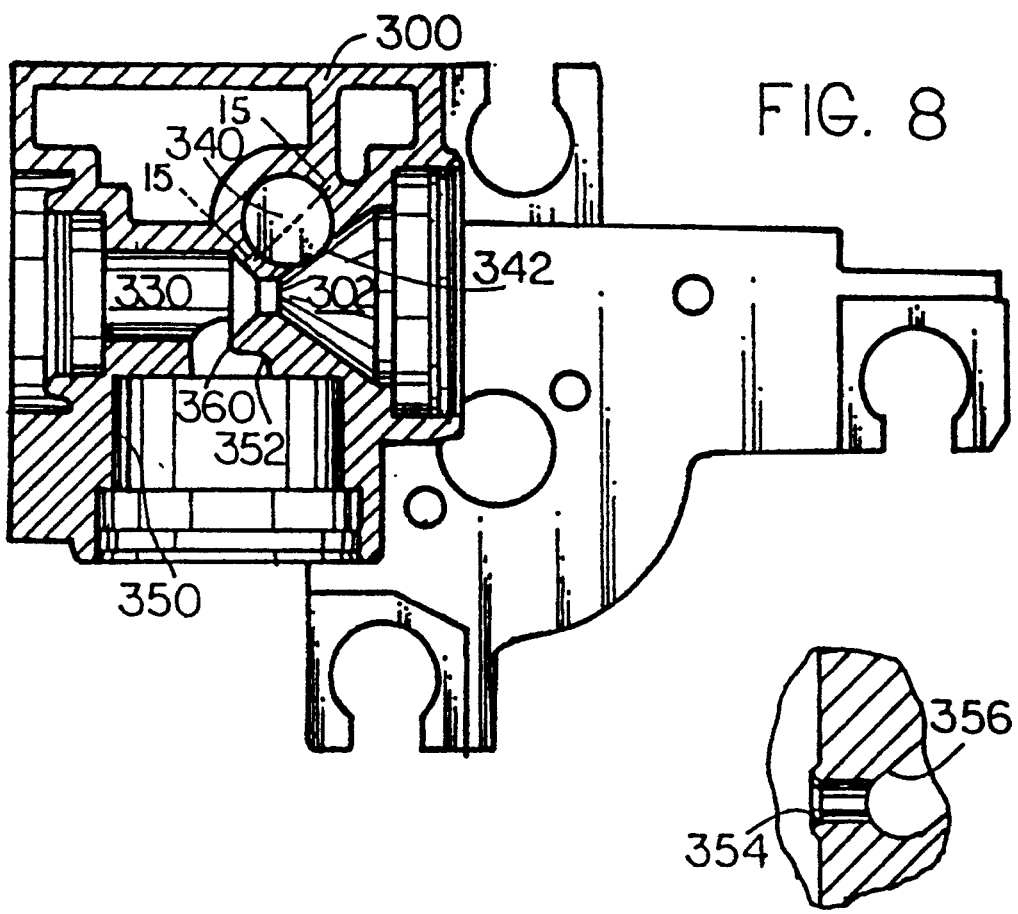
FIG. 8
FIG. 12
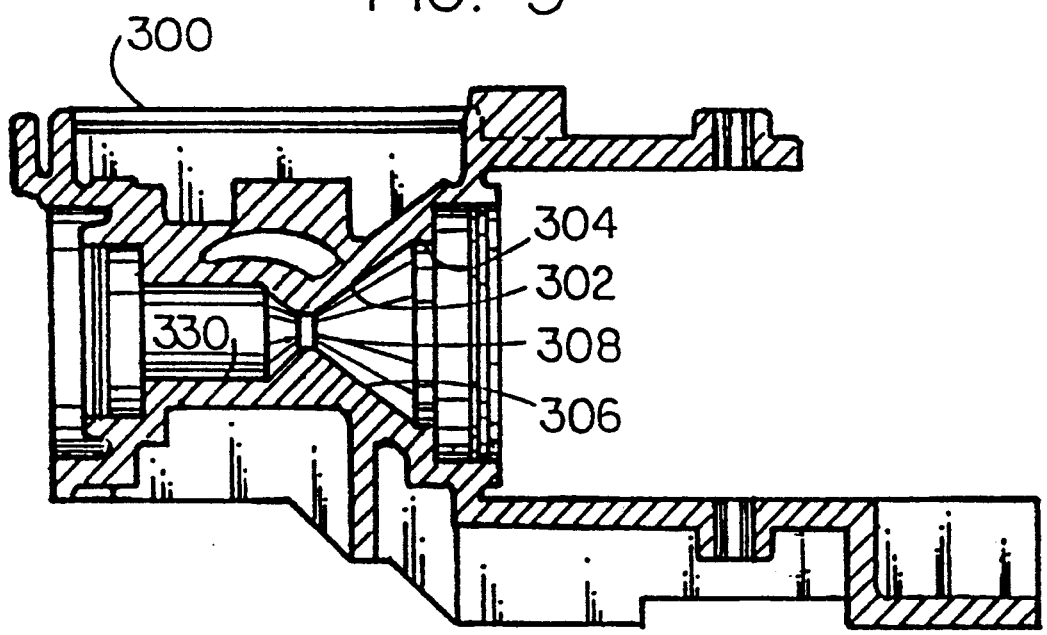
FIG. 9

ORAL HYGIENE APPLIANCE

SPECIFICATION

The present invention pertains to oral hygiene appliances. More particularly, it relates to an oral hygiene center in which are included both an electric toothbrush together with a plurality of individual brushes as well as a handle in which is inserted a selected one of several stored jet tips for the delivery of pulses of water to the teeth and gums of the user.

Oral hygiene appliances of a kind which deliver to the teeth and gums of the user jet pulses of water have come into widespread use since their introduction into the marketplace well over twenty-five years ago. An example of one quite successful early unit is that disclosed and claimed in U.S. reissue patent RE27274 to Mattingly and assigned to the same assignee as the present application. In the appliance of that patent, a cabinet encloses an electric motor and a pump assembly which feeds the jet pulses through a flexible hose to the base of a handle into which is fitted a jet tip. Water inletted to the pump is stored in a reservoir which in use mounts on top of the cabinet but which for storage is invertible so as to cover the unit and also the stored jet tip and its hose. That appliance also includes in association with its pump a control for adjusting the level of pressure at which the pulses are delivered. Many of the principles associated in that patent still find use today.

Over the intervening years numerous additional patents have issued with respect to oral hygiene appliances having improvements or worthwhile additional features over the basic approach and a number of different manufacturers have entered the field. One quite successful newer version again introduced by applicants' assignee is that disclosed and claimed in U.S. Pat. No. 4,989,590. Indeed, certain features of that patent continue forward into the appliance to which the present application is directed.

At the same time, the use of the more ordinary toothbrush has continued to be desirable both separately and in addition to use of oral irrigators of the kind discussed above. One version of toothbrush which has proved to be quite popular is that in which the brushhead is driven by an electric motor energized by a battery contained along with the motor in an elongated handle. Desirably, the unit when stored sits down into a charging base as to enable recharging of the battery. One attractive form of electric toothbrush having all of the basic features necessary is that disclosed and claimed in U.S. Pat. No. 4,374,354-Petrovic. However, a preferred form of electric toothbrush, as such, is that disclosed and claimed in the co-pending application Ser. No. 08/080,003 filed Jun. 21, 1993 by Andrew Serbinski, Roberta L. Callaghan and Steve O. Mork and assigned to the same assignee as the present application.

The usage of both a toothbrush and an oral irrigator continues to be recommended at least for most people. It was heretofore proposed and even accomplished that a unitary assembly include both an oral irrigation appliance and a rechargeable electric toothbrush. It is with that overall unit user's convenience in mind that the present invention is presented in the form of such a combination oral hygiene center which includes both an electric toothbrush and a complete oral irrigator. However, either the electric toothbrush or the oral irrigator to be presented may be manufactured and sold as a separate item.

It is a general object of the present invention to provide a new and improved oral hygiene appliance having a jet tip handle and mounting arrangement which is advantageous.

Another object of the present invention is to provide a new and improved oral hygiene appliance having an electric toothbrush and an associated storage for spare brushheads which afford user convenience.

A further object of the present invention is to provide an oral hygiene appliance of the kind having an invertible reservoir-cover and in which reservoir stability is enhanced.

A more detailed object of the present invention is to provide a new and improved handle in which a jet tip is received and mounted.

Yet another object of the present invention is to provide a new and improved oral hygiene appliance which includes a highly effective and durable pumping mechanism.

Still another more detailed object of the present invention is to provide for an oral hygiene appliance a new and improved pressure control which also serves to limit excessive pressure.

In accordance with one aspect of the present invention, an oral hygiene appliance includes a horizontally elongated base upstanding from which is a cabinet having top, front and rear vertical walls. A pressure-control dial is exposed on a laterally central portion of the front wall, while a pair of recesses are formed in respective opposite terminal portions of that wall on either side of the central portion. Formed individually into the base within those recesses are several seats each receptive of the base portion of a tubular jet tip. An inlet is defined in the top wall. A cover is shaped to envelope the cabinet and enclose the recesses, the dial and the inlet with the cover being invertible to serve as a reservoir and having in its horizontal wall a valve operable to release water into the inlet when the cover is inverted and mounted atop the top wall. A pump is disposed within the cabinet and responds to a pressure control for delivering water from the inlet. Finally, a handle is receptive of one of the jet tips to enable delivery of the water to a point of use.

Desirably, the thickness of the cabinet between the front and rear walls gradually diminishes from the middle toward each lateral end and the corresponding thickness of the cover correspondingly diminishes from its middle toward its lateral end. Preferably, a valve is supported within a structure that projects outwardly from the horizontal wall in which case the cover includes forward and rearward walls together with a horizontal wall in which the valve is mounted and in which case the forward and rearward walls project above that horizontal wall at least as far as the structure. It is also preferable that the upper edge portions of the front and rear walls define insets and that the forward and rearward walls project beyond the horizontal wall and seat in the insets when the cover is inverted and mounted atop the top wall.

In another aspect of the present invention an electric toothbrush assembly includes an elongated generally-tubular housing. A battery, a motor and a motion translator are all disposed within the housing with the translator having a fitting exposed through one end of the housing. Formed in a horizontal base portion is a well of a size to receive and seat a terminal portion of the housing including the other end thereof. Disposed atop the base to the rear of the well is a pedestal on top of which are located a plurality of mountings individually located in respective different positions. Another plurality of mountings individually are located in respective different positions on top of the base alongside the well and in front of the pedestal. Finally, a plurality of brushes each has a shank with bristles distributed over one end portion thereof with the other end portion defining a coupling selectively engageable with different ones of the fitting and the mountings.

In a further aspect of the present invention an oral hygiene appliance includes a horizontally-elongated base upstanding from a portion of which is a cabinet which encloses an oral irrigation pump unit. An elongated handle has secured at one end a jet tip to enable delivery and from the other end of which there emerges a flexible hose receptive of water from the pump unit; a hollow boss upstands from a portion of the base and is disposed to one side of the cabinet with the interior of the boss being sized to accept the other end of the handle. A cylindrical wall upstands from that portion of the base and is spaced around the boss by an amount sufficient to allow coiling of the hose as the other end of the handle is seated in the boss, Desirably, that other end of the handle includes a longitudinal slot in its interior and alignable with a rib which projects laterally from the interior wall of the boss for captivation of the rib. Also desirably a relief is defined in the upper end surface of the boss and into which a portion of the hose rests as said handle seats in the boss.

In accordance with yet another aspect of the present invention an oral hygiene appliance delivery system includes a jet tip with an elongated hollow shank terminating in its end portion opposite its output end with a circumferentially-faceted portion beyond which is defined a neck and further beyond which is a nipple coupled to a conduit, A valve operator accessible on the housing is operable to close the conduit, Another nipple is secured to the end of the conduit beyond that operator and a flexible hose is coupled between the other nipple and a source of irrigation, The invention also relates to an oral hygiene appliance having a housing into which water is supported and from which the water is delivered through a flexible hose to a point of use. A pumping chamber is defined in the housing to have a mouth joined by a side wall to a neck, A flexible diaphram is sealingly disposed across the mouth, A rod at one end secured centrally to the diaphram is at its other end driven in reciprocation, There is an outlet from the housing and a passage between the neck and the outlet. In that passage is a first check valve which permits water flow only toward the outlet, There also is an inlet into the housing and a duct between the inlet and an opening through the sidewall into the chamber. A second check valve in that duct permits water flow only toward the chamber.

In carrying forward the invention, one outwardly-facing well is defined in the body. A bore is formed in the bottom of the well in which bottom is also an opening. There is a passageway from the opening into the sidewall of the pumping chamber. A piston is disposed in the bore. A port through the housing from the head on one end of the piston leads into the passage at a location beyond the outlet from the seat of the first check valve. A radius variable rotatable and axially moveable cam is defined in the other end of the piston and is seatable within the well with the cam having a lateral flat normally covering said opening. A spring urges the cam flat closed against the opening but enables pressure beyond a limit in the passage to move the piston and bleed back through the passageway. A portal formed in the side wall of the well is in alignment with the cam. A pathway is defined in the housing and leads from the portal to the inlet. Finally, a control knob couples rotation to the cam in variation of the amount of pressure bled back from the chamber through the pathway to the inlet. In a preferred further implementation, the well further includes a cup-shaped collar having the portal defined in a side wall thereof. Included in the bottom wall of the collar are holes corresponding to the bore and the opening. There is a disc secured on the outer side of the bottom wall and it has cylindrical ports individually seated in respective ones of the holes in ultimate delineation of the bore and the opening.

The features of the present invention which are believed to be patentable are set forth with particularity in the appended claims. The organization and manner of operation of the invention, together with further objects and advantages thereof, may best be understood by reference to the following description taken in connection with the accompanying drawings, in the several figures which like reference numerals identify like elements and in which:

FIG. 1 is a partially-exploded isometric view of an oral hygiene center with certain of the accessory components removed and with an invertible cover oriented to its storage position;

FIGS. 2A and 2B, with the former above the latter, together constitute an exploded isometric view of the lower portion of the oral hygiene center shown in FIG. 1;

FIG. 3 is a fragmentary front elevational view of one end portion of the center shown in FIG. 1 and with an accessory component added;

FIG. 4 is a left side elevational view of the base portion of the oral hygiene center shown in FIG. 1 but with additional accessory components added and with a showing in phantom of the cover of FIG. 1 inverted to serve as a reservoir;

FIG. 4A is a rear elevational view of a component shown in FIG. 4;

FIG. 4B is a bottom plan view of the component shown in FIG. 4A;

FIG. 5A is a fragmentary isometric view of a portion of FIG. 1 associated with an accessory part;

Figure 2A:
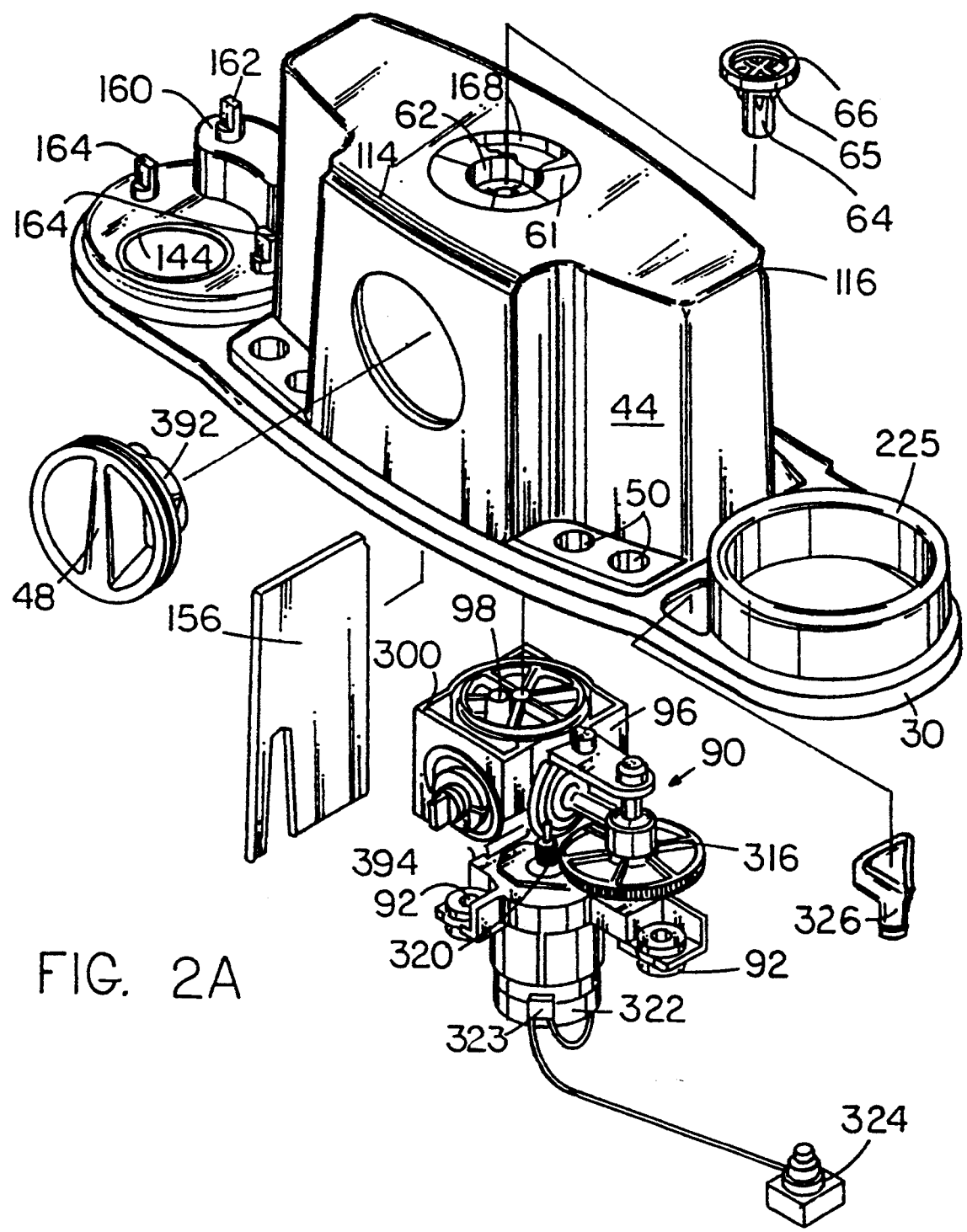
Figure 2B:
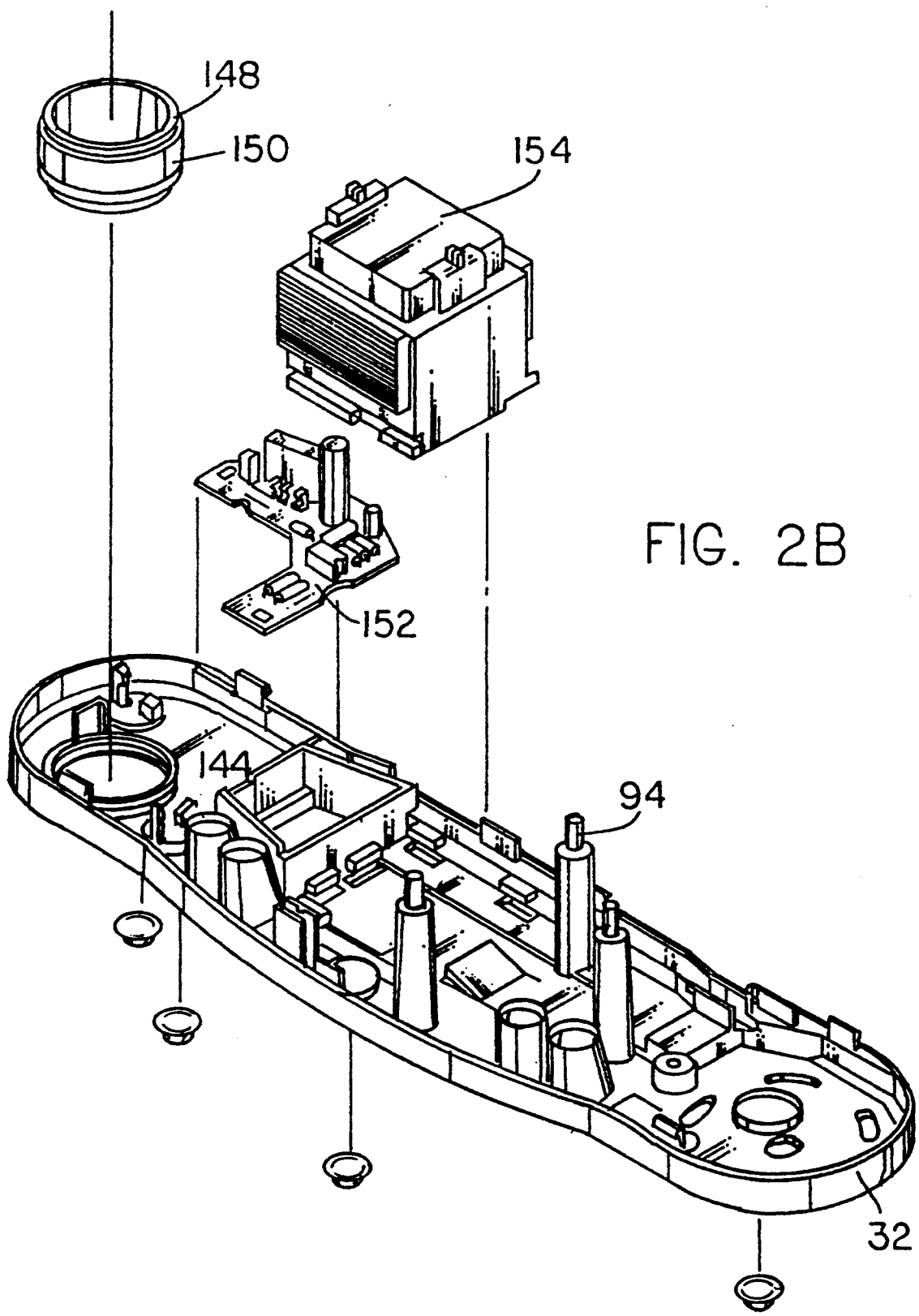
Figure 5:
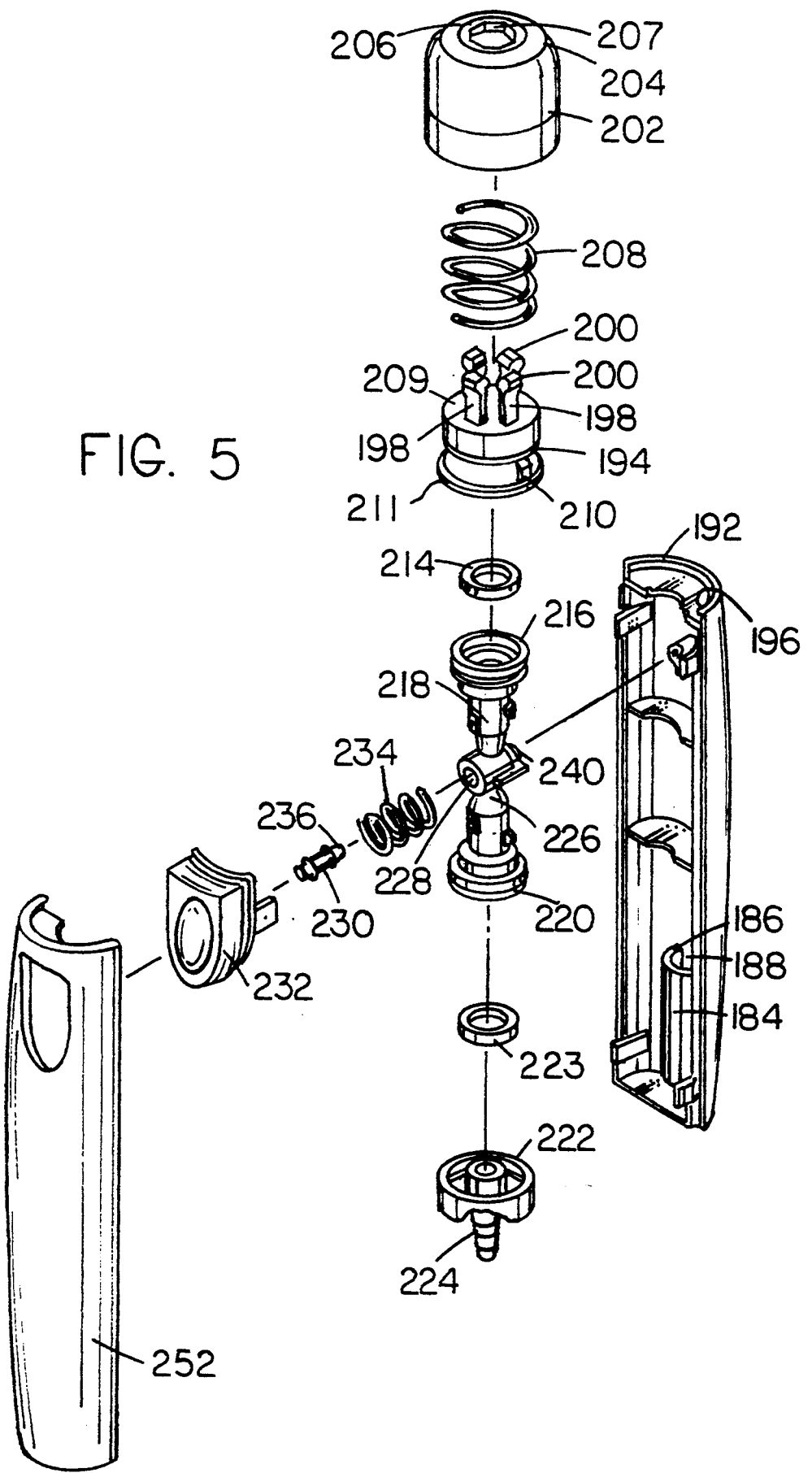
FIG. 5 is an exploded isometric view of another accessory component which is shown in FIG. 1.
Figure 6:
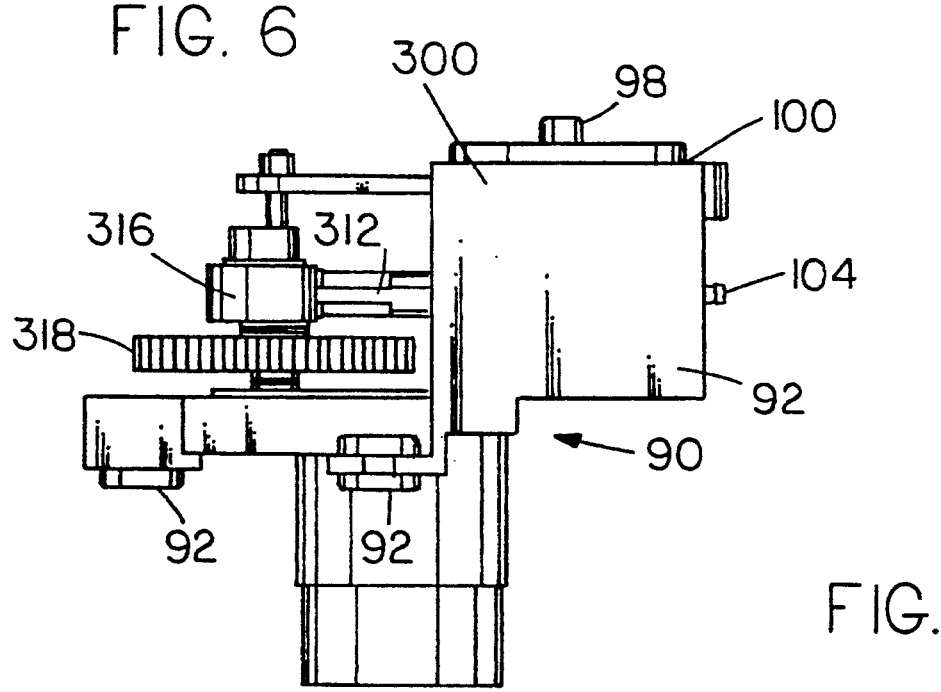
FIG. 6 is a rear elevational view of a motor and pump assembly shown in FIG. 2A.
Figure 7C:
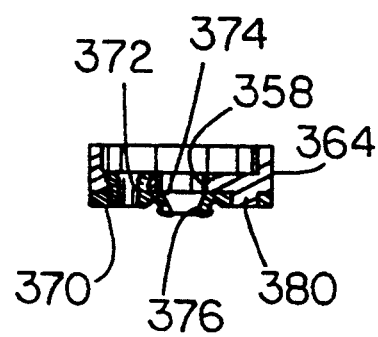
Figure 5B:
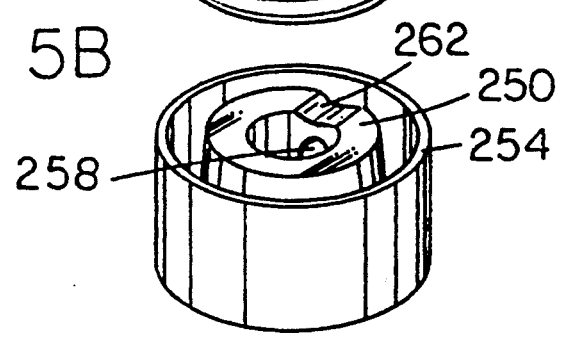
FIG. 5B is a fragmentary exploded isometric view of a portion of FIG. 5A.
Figure 7A:
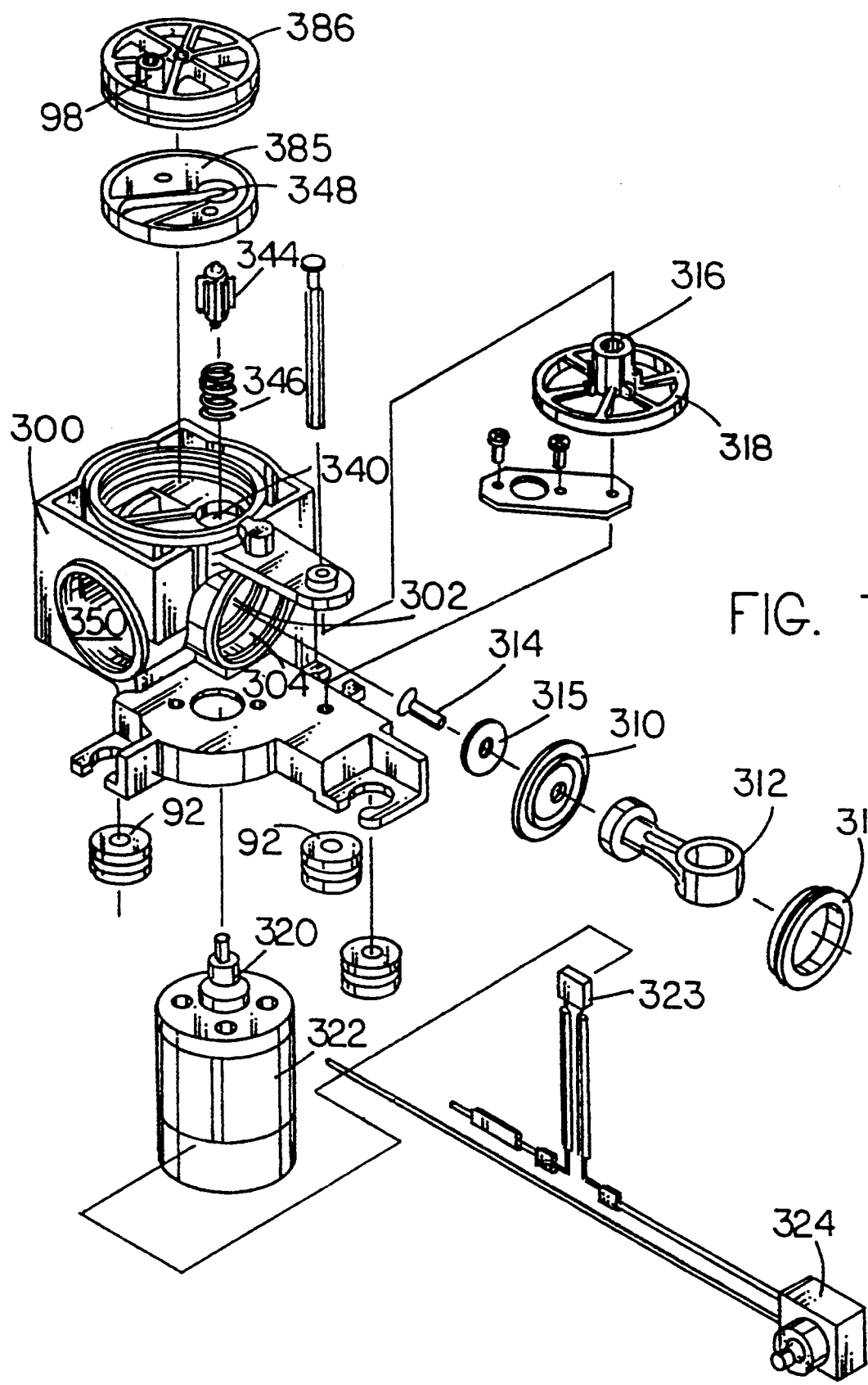
Figure 10:
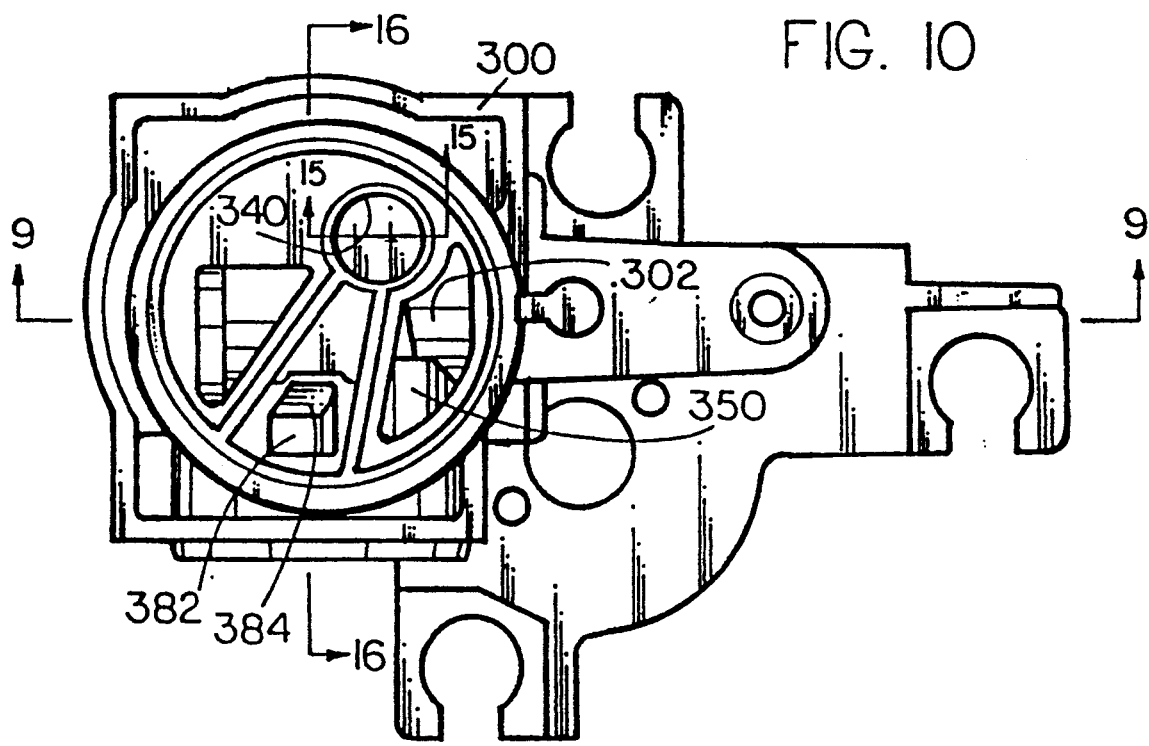
Figure 11:
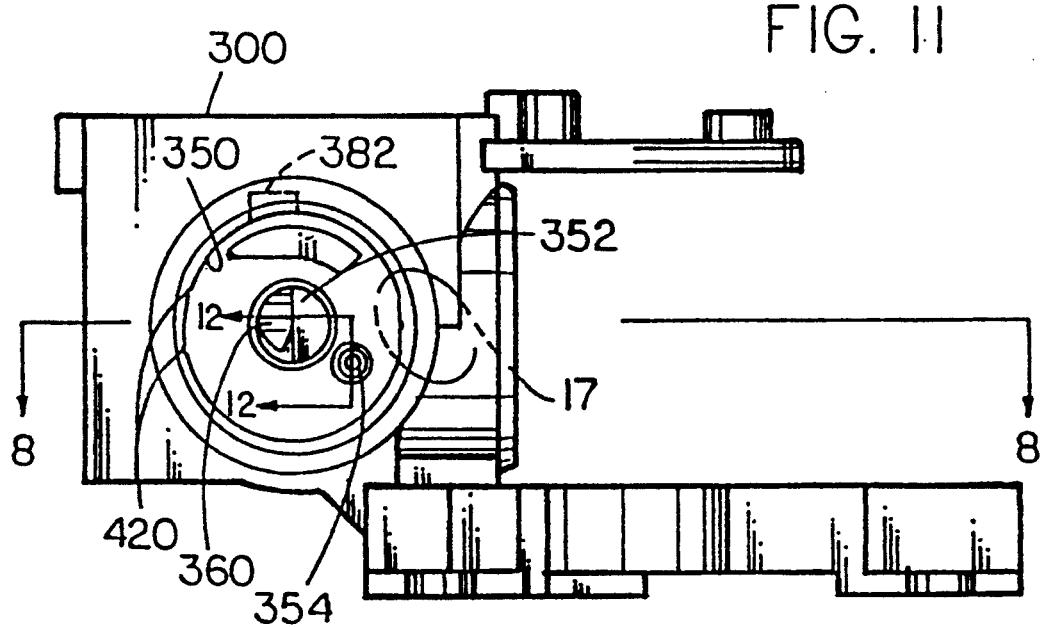
Figure 13:
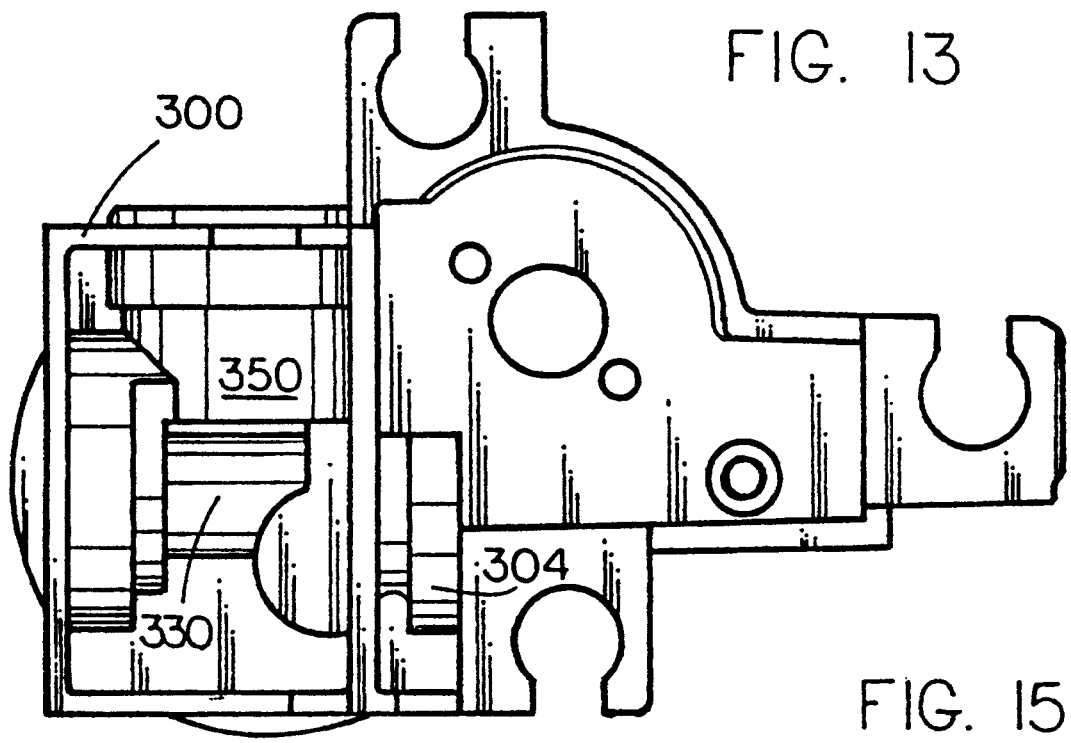
Figure 15:
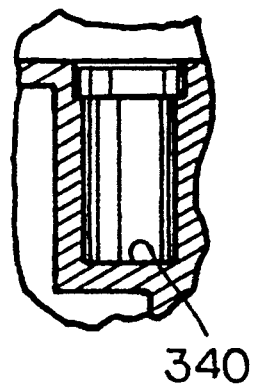
Figure 14:
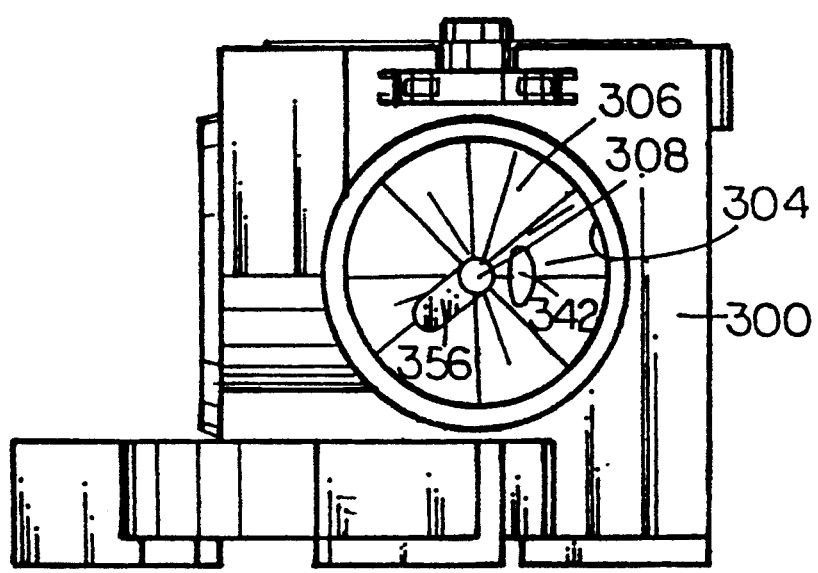
Figure 16:
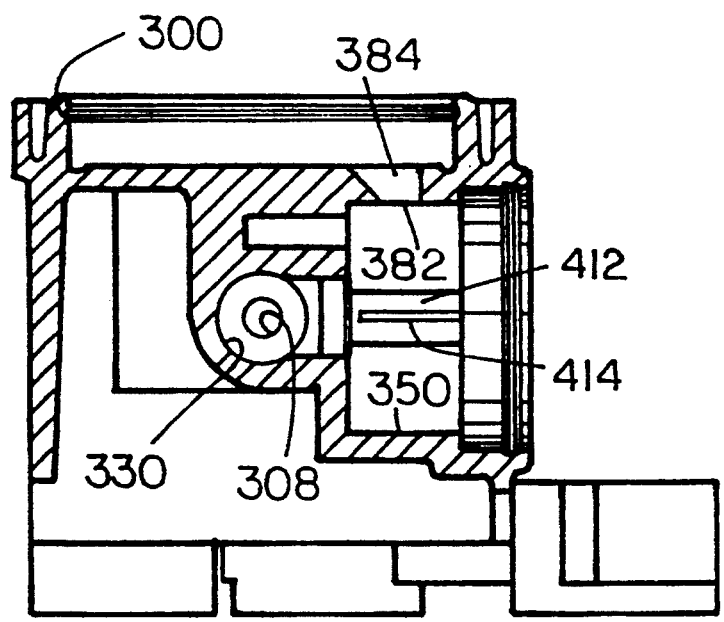
Figure 17:
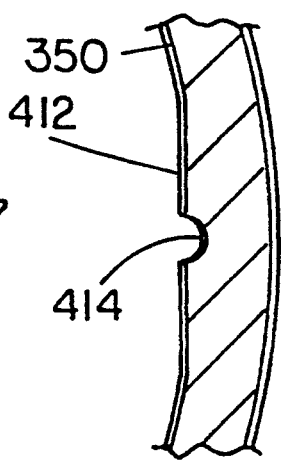

FIGS. 7A and 7B together constitute an exploded isometric view of the pump assembly of FIG. 6;

FIG. 7C is a cross-sectional view of an assembly shown in FIG. 7B:

FIG. 8 is a cross-sectional view taken along the line 8—8 of FIG. 11;

FIG. 9 is a cross-sectional view taken along the line 9—9 in FIG. 10;

FIG. 10 is a top plan view of a pump housing included in the assembly of FIG. 6;

FIG. 11 is a front view of that pump housing;

FIG. 12 is a fragmentary cross-sectional view taken along the line 12—12 in FIG. 11;

FIG. 13 is a bottom plan view of the pump housing of FIG. 10;

FIG. 14 is a right side elevational view of the pump housing including in the pump assembly of FIG. 2A;

FIG. 15 is a fragmentary cross-sectional view taken along the line 15—15 in FIG. 10;

FIG. 16 is a cross-sectional view taken along the line 16—16 in FIG. 10 and rotated by 90°;

FIG. 17 is a fragmentary magnified view of portion 17 of FIG. 11;

FIG. 18 is an enlarged front-elevational view of a component shown in FIG. 7B; and FIG. 19 is a right side-elevational view of the component shown in FIG. 18.

An oral hygiene center 20 includes a horizontally elongated base 22 upstanding from which is an oral hygiene appliance or irrigator 24 with its handle 26. Also upstanding from base 22 when in a stored position is an electric toothbrush handle 28. To enable access during assembly and for subsequent repair, base 22 is fabricated in upper and lower halves 30 and 32 which upon assembly are fastened together.

Irrigator 24 includes a cabinet 34 upstanding from base 22 and having a top wall 36, a front wall 38 and a rear wall 40. A pair of recesses 42 and 44 individually are formed in respective opposite terminal portions of front wall 38 on either side of its central portion 46. A pressure control dial 48 is positioned through central portion 46.

A plurality of seats 50 are formed individually into base 16 within recesses 42 and 44 and each is receptive of a nipple 52 which projects downwardly from a ferrule 54 from which upwardly projects a shank 56 bent laterally to one side at its tip 58 through which is formed a small orifice. It is customary to refer to the entire article including shank 56 as a "jet tip".

An inlet 60 is formed centrally into top wall 36 and includes a circular depression 61 downwardly from which depends a well 62. Protruding down through a hole 63 in the bottom of well 62 is a hollow post 64 the upper end of which flares into a cup 65 within which upstand several rigid fingers 66. Encircling depression 61 and depending downwardly from the underside of top wall 36 is a collar 168.

A cover 72 is shaped to envelope cabinet 34 and enclose recesses 42 and 44, dial 48 and inlet 60. Cover 72 is invertible to serve as a reservoir and thus has in its horizontal wall 74 a valve 76 operable to release water into inlet 60 when cover 72 is so inverted and mounted atop top wall 36. Valve 76 includes an upwardly projecting boss 78 through an opening 80 in the bottom of which is mounted a valve member 82. Valve member 82 is made of a resilient material. Across its upper end of a central leg 83 is a flange 84 and projecting laterally from the lower end of leg 83 are bars 86 disposed beneath opening 80. With cover 72 removed from cabinet 34 and in its inverted position, the pressure of water on flange 84 supplements a preloading molded into valve member 82 to maintain sealing closure of valve 76. But when the inverted cover is mounted atop cabinet 34 fingers 66 on hollow post 64 press upwardly against valve member 82 and cause flange 84 to be pushed away from its seat in the surrounding interior portion of horizontal wall 74. Desirably, wall 74 slopes toward opening 80 to assist in complete drainage. This manner of use and operation of a reservoir-cover is fully explained in the aforesaid patent No. RE27274. The principles behind, alternatives in specific structure of and manner of operation of valve 76 are fully discribed in the aforesaid U.S. Pat. No. 4,989,590.

Disposed within cabinet 34 is a motor and pump assembly 90 mounted by grommets 92 on the free ends of posts 94 upstanding from base 22. A pump 96 has an inlet 98 coupled to the lower end of hollow post 64 to receive water through valve 76. Collar 168 seats on a rim 100 surrounding inlet 98 to stabilize the mounting of assembly 90 on posts 94. Pump 96 also includes an outlet 104 coupled by a flexible hose 106 into the bottom of handle 26. Handle 26 is receptive of one of jet tips 56 so as to enable the delivery of water from the reservoir through the pump to a point of use.

The thickness of cabinet 34 between its front and rear walls 38 and 40 gradually diminishes from the middle toward each lateral end of cabinet 34. Similarly, the corresponding thickness of cover 72 diminishes from its middle toward the lateral ends thereof. Reservoir valve boss 78 projects outwardly from horizontal wall 74 of cover 72. Providing clearance upon mounting, forward wall 110 and rear wall 112 of cover 72 project above horizontal wall 74 at least as far as boss 78. This adds stability to cover 72 while inverted to serve as a reservoir. Additionally serving that purpose, the upper edge portions 114 and 116 of front wall 38 and rear wall 40 define insets. Ribs 118 and 120, formed by the projections of the front and rear walls of cover 72 beyond its horizontal wall 74, seat on the ledges formed by insets 114 and 116 when cover 72 is inverted and mounted atop top wall 36 so as to serve as a reservoir.

The electric toothbrush of handle 28 may take the form of several presently known such appliances so that the particulars of its construction are not of the essence of the present invention. Nevertheless, it is presently preferred to employ that certain electric toothbrush described and claimed in the aforementioned co-pending application Ser. No. 08/080,003 filed Jun. 21, 1993, now U.S. Pat. No. 5,341,534. That application is incorporated herein by reference for the convenience of the reader.

The toothbrush handle 28 includes an elongated generally tubular housing 130 within which are distributed a rechargeable battery 132, an electric motor 134 energized by the battery and a motion translator 136 driven by the motor. All are disposed within housing 130 with motion translator 136 having a fitting 140 exposed through nose end 142 of housing 28. In base 22 is a well 144 of a size and shape to receive and seat a terminal portion 146 of housing 130. Encircling well 144 on a bobbin 148 is a charging coil 150 connected to a conventional energizing circuit on a board 152 located in base 22 and fed from a transformer 154 connected to a suitable household power receptacle for recharging battery 132. A rigidifying barrier wall 156 separates board 152 and transformer 154.

A pedestal 160 is disposed atop base 22 in a position to the rear of well 144. Spaced lengthwise of base 22 are a pair of mountings 162 individually located in respective different positions on top of pedestal 160. Another pair of mountings 164 are individually located in respective different positions on top of base 22 alongside well 144 and in front of pedestal 160. A plurality of brushes 166 each has a shank 170 with bristles 172 distributed over the free end portion thereof. The other end portion of each shank defines a coupling 174 engageable upon those mountings or upon fitting 140 projecting beyond nose 142 of toothbrush 28. Pedestal 160 serves to position the rearmost stored toothbrushes at a higher elevation. This makes it easier for the user in front of the oral hygiene center to reach behind handle 28 in a stored position and retrieve or depose either one of those rearward toothbrushes.

The delivery system as indicated uses a jet tip having a hollow shank 56 with an orifice through output end 58. At the other end beyond a ferrule 54 are an outward-facing plurality of six circumferentially-spaced facets 180, Beyond facets 180 is a neck 182 and further beyond neck 182 is terminal nipple 52. Handle 26 at its lower end has an elongated indentation 184 severed at one end 186 to leave an opening 188 from which emerges hose 106.

Projecting axially outward from the other end 192 of handle 26 is a collar 194 captivated in place by an in-turned rim 196 at one end of the collar and from the other end of which project a circumferentially-spaced plurality of four flexible fingers 198 each of which ends in a nub 200 which seats into neck 182 on shank 56.

Surrounding collar 194 and fingers 198 is a cap 202 having an end 204 in which is formed an opening 206 the inner wall of which defines a set of facets 207 which match and mate with facets 180 on shank 56. A spring 208 is compressed between an internal lip in cap 202 around opening 206 opposite nubs 200 and a shoulder 209 defined around collar 194 at fingers 198. A pair of oppositely disposed keys 210 are struck into the wall of collar 194 and may be depressed to unlock cap 202 by projecting into a gap between cap 202 and rim 196. A flange 211 on collar 194 is otherwise locked in place by an in-turned rim around the interior of cap 202 at its open end.

Nipple 52 on the end of shank 56 seats through an O-ring 214 into a bell 216 formed on the upper end of a conduit 218. Another bell 220 at the lower end of conduit 218 seats a fitting 222 on an O-ring 223 from which projects a nipple 224 on which one end of hose 106 is affixed. Centrally located in conduit 218 is a necked-down barrel 226 in which is defined a bore 228 that receives a valve rod 230 on the other end of which is secured a pushbutton 232 biased outwardly by a spring 234. On depression of pushbutton 232 the inner end 236 of rod 230 moves inwardly to close an interior passage through conduit 218 and thus cut off the fluid flow. A boss 240 serves to rigidify conduit 218 at barrel 226 and mount conduit 218 within handle 26.

A hollow boss 250 upstands from a portion of base 16 located to one side of cabinet 34. Boss 250 is sized to accept the lower end 252 of handle 26. A cylindrical wall 254 within a ring 255 on base 22 is spaced around boss 250 by a distance sufficient to accommodate a preset coiled portion 256 of hose 106 as handle 26 is seated in boss 250. A rib 258 is formed vertically on the interior wall of boss 250 and is captivated within indention 184 defined in the lower end of handle 26. A relief 262 is defined in the upper end surface of boss 250 and serves to accept an outturned portion of hose 106 as handle 26 seats into boss 250.

Pump 96 includes a housing 300 into which water is supplied to an inlet 98 and from which water is delivered from outlet 104 through hose 106. Defined within the housing is a funnel-shaped pumping chamber 302 having a mouth 304 joined by a side wall 306 to a neck 308. A flexible diaphram 310 is seated by a retainer 311 and disposed across mouth 304. A rod 312 at one end is secured centrally to diaphram 310 by a screw 314 through a washer 315 and at its other end is driven in reciprocation by a rod bearing 316 mounted eccentrically on a driven gear 318. Driven gear 318 is rotated by a driving gear 320 powered in rotation by an electric motor 322. A thermal sensor 323 is connected in series with a switch 324 between one terminal of the motor and circuit board 152. Accessible on top of base 22 is a switch operator 326 for switch 324.

A passage 330 leads from neck 308 to outlet 104. Disposed within passage 330 is a check valve 332 biased to a normally closed position by compression spring 334. A duct 340 communicates between inlet 98 and an opening 342 in side wall 306 into chamber 302. Another check valve 344 biased by a compression spring 346 is disposed in duct 340 and closes upon a seat 348 to permit water flow only toward chamber 302.

Defined in the body of housing 300 is a well 350 into the bottom of which is formed a bore 352 to one side of which is also formed an opening 354. A passageway 356 leads from opening 354 into side wall 306 of chamber 302. A piston 358 is disposed in bore 352. A port 360 is formed through the housing from the head end of piston 358 into passage 330 at a location toward outlet 104 from the seat of check valve 332 at neck 308.

A radius-variable rotatable and axially movable cam 362 is defined on the other end of piston 358 and is seatable within a cam retainer 364 in turn seated in well 350. Cam 362 has a lateral flat 366 which normally is aligned in covering relationship to opening 354. A spring 368 urges cam 362 toward opening 354. Retainer 364 is affixed to a disc 370 in which is found an opening 372 aligned with opening 354 and which also has a central opening 374 bounded by an inner lip seal 376 that is received on piston 358. A series of posts on retainer 364 seat in corresponding holes 380 in disc 370 to secure against relative rotation and control compression on disc 370. A portal 382 is formed into the side wall of well 350 in alignment with cam 362, and there is a pathway 384 defined in housing 300 that leads from portal 382 back to inlet 98 by way of a channeling disc 385 beneath a closure 386 from which inlet 98 projects.

Dial 48 has rearward projecting fingers 392 which grasp a spade 394 that projects forward from a stem 396. Stem 396 is splined to cam 362 so that rotation of dial 48 to adjust the pressure setting rotates cam 362 in order to vary the rotational position of flat 366.

Rotation of dial 48 and consequent rotation of cam 362 thus serves to vary the amount of pressure bled back from pumping chamber 302 by way of pathway 384 to inlet 98. It will be seen that retainer 364 is in the shape of a cup-shaped collar. Defined in a side wall thereof is a port 398 aligned with portal 382 and the bottom wall thereof has holes corresponding to bore 352 and opening 354. Disc 370 is secured on the inner side thereof and has corresponding pores or openings individually seated in respective ones of matching holes or openings and in ultimate delineation of the central bore and the lateral bypass opening. A cap 400 enveloped over stem 396 and spring 366 serves to mount the assembly of the cam, retainer and disc within well 350. As illustrated, O-rings 402 and 404 complete the necessary seals.

Disc 370 is of elastomeric material. Holes 380 are distributed circumferentially in a pattern which matches that of three posts which project outwardly from the closed end face of retainer 364 and the holes are sized to press fit tightly on the posts. Opening 372 is in the form of a hollow post or button that projects away from the face of disc 370 a distance sufficient to penetrate through a mating hole 365 in the closed end face of retainer 364 and flare into a seal against which the facing side of land 366 is pressed.

Lip 376 projects away from disc 370 and defines a resilient seal around piston 358 which protrudes through a central opening 367 in the closed end face of retainer 364. The surface of cam 362 varies in level of depth below land 366 by an amount selected to yield a variation in back flow which is proportional to the degree of rotation of cam 362 by dial 48.

In operation, a turning of dial 48 to rotate cam 362 serves to vary the proportion of water diverted back from the outlet directly to the inlet and thus back into the connected reservoir. There is an approximately linear variation of pressure in response to a given amount of rotation of dial 48. When, however, cam 362 is oriented to close and thus block portal 382, the outlet pressure in passage 330 is communicated through port 360 to the face of piston 258. When that outlet pressure exceeds a predetermined level, piston 258 forces the body of cam 362 to move outwardly at which time cam flat 366 pulls away from covering relationship to opening 354. The pressure immediately is diminished by a direct short circuit from passage 384 through passageway 356 back into the pumping chamber. That action serves to guard against a possibly uncomfortable pressure level as otherwise might occur when dial 390 is set at the maximum pressure level. It also serves to limit pressure to the pump and conserve energy when pushbutton 232 is depressed.

As an aid to correct assembly and also to ensure a proper relative relationship between different parts, the different molds are fabricated to include keys or guides. For example, a flat 412 on one portion of the side wall of well 350 includes an axially-directed groove 414. Groove 414 and flat 412 mate with a corresponding rib 416 and a land 418 on the peripheral circumference of retainer 364. Opposite groove 414 on the other side of well 350 are a circumferentially-spaced pair of additional grooves 420 which cooperate with correspondingly-placed ribs on the outer side wall of retainer 364.

Desirably, great care is to be taken in choosing the characteristics and dimensions of the different parts. For example, the diameter of the coil in hose 106 should be selected to maximize performance in terms of pressure while at the same time avoiding a diameter which would result in a resonant mode for the hose. Disc 370 in the pressure control is formed of an elastomeric material not only so that it may serve well as a bypass seal but also so that lip 376 serves to dampen the motion of piston 358. That damping reduces what otherwise would be a requirement for a larger preload from spring 368 and that, in turn, assists in minimizing power consumption. Lowered power consumption helps to ensure that the appliance properly works in the so-called shaver sockets found in some European countries.

Handle 26 represents an improvement by reason of its use of a positive locking mechanism. That is, the O-ring which serves as a seal is separated from the fingers which lock the jet tip in place. The result is an easy release by simple actuation of the collet while yet maintaining a secure fit during use.

It may be noted that valve 230 within handle 26 is constructed to fully retract from the flow path therethrough. That serves the attainment of a very low pressure drop in use.

The formation of pumping chamber 306 in the shape of a funnel facilitates priming and also the purging of air from the unit during the initiation of use. By selecting the use of a diaphram together with the pump guards against the development of leaks from the pump unit as otherwise may be found to be the case when the more conventional piston pump is employed.

Shown in the overall has been a complete oral hygiene center having both an electric toothbrush and an oral irrigator. When desired, of course, those two sections may be accommodated as entirely and individually separate products. In any case, careful attention has been given to the location of the various different components with the objective of maximizing consumer convenience and ease of use.

While a particular embodiment of the invention has been shown and described, and various alternatives have been discussed, it will be obvious to those skilled in the art that changes and modifications may be made without departing from the invention in its broader aspects. Therefore, the aim in the appended claims is to cover all such changes and modifications as fall within the true spirit and scope of that which is patentable.

We claim:

1. An oral hygiene appliance comprising:
   a horizontally elongated base;
   a cabinet upstanding from said base and having top, front and rear vertical walls;
   a pressure control in said cabinet;
   a pressure-control dial exposed on a laterally central portion of said front wall;
   a pair of recesses individually formed in respective opposite terminal portions of said front wall on either side of said central portion;
   a plurality of seats formed individually into said base within said recesses and each receptive of the base portion of a tubular jet tip;
   a plurality of said jet tips;
   an inlet defined in said top wall;
   a cover shaped to envelope said cabinet and enclose said recesses, said dial and said inlet, said cover being invertible to serve as a reservoir and having in a horizontal wall a valve operable to release water into said inlet when said cover is inverted and mounted atop said top wall;
   a pump disposed within said cabinet and responsive to said pressure control for delivering water from said inlet;
   and a handle receptive of one of said jet tips to enable delivery of said water to a point of use.

2. An oral hygiene appliance as defined in claim 1 wherein the thickness of said cabinet between said front and rear walls gradually diminishes from the middle toward each lateral end thereof and in which the corresponding thickness of said cover matingly diminishes from the middle toward the lateral ends thereof.

3. An oral hygiene appliance as defined in claim 1 in which said valve is supported within a structure which projects outwardly from said horizontal wall and in which said cover includes forward and rearward walls together with said horizontal wall in which said valve is mounted, with said forward and rearward walls projecting above said horizontal wall at least as far as said structure.

4. An oral hygiene appliance as defined in claim 1 in which the upper edge portions of said front and rear walls define insets and in which said forward and rearward walls project beyond said horizontal wall and seat in said insets when said cover is inverted and mounted atop said top wall.

5. An oral hygiene appliance comprising:

a horizontally elongated base;

a cabinet upstanding from said base and having top, front and rear vertical walls;

a pressure control in said cabinet;

a pressure-control dial exposed on a laterally central portion of said front wall;

a pair of recesses individually formed in respective opposite terminal portions of said front wall on either side of said central portion;

a plurality of seats formed individually into said base within said recesses and each receptive of the base portion of a tubular jet tip;

a plurality of said jet tips;

an inlet defined in said top wall;

a cover shaped to envelope said cabinet and enclose said recesses, said dial and said inlet, said cover being invertible to serve as a reservoir and having in a horizontal wall a valve operable to release water into said inlet when said cover is inverted and mounted atop said top wall;

a pump disposed within said cabinet and responsive to said pressure control for delivering water from said inlet;

a handle receptive of one of said jet tips to enable delivery of said water to a point of use;

a seat for said handle located on said base at one side of said cabinet;

an elongated generally tubular housing;

a battery, a motor energized by said battery and a motion translator driven by said motor all disposed within said housing with said translator having a fitting exposed through one end of said housing;

a well disposed in said base in a location opposite said cabinet from said seat and of a size to receive and seat a terminal portion of said housing including the other end thereof;

a pedestal disposed atop said base to the rear of said well;

a plurality of mountings individually located in respective different positions on top of said pedestal;

another plurality of mountings individually located in respective different positions on top of said base alongside said well and in front of said pedestal;

and a plurality of brushes each having a shank with bristles distributed over one end portion thereof and with the other end portion defining a coupling selectively engageable with different ones of said fitting and said mountings.

6. An oral hygiene appliance comprising:

a horizontally elongated base;

a cabinet upstanding from said base and having top, front and rear vertical walls;

a pressure control in said cabinet;

a pressure-control dial exposed on a laterally central portion of said front wall;

a pair of recesses individually formed in respective opposite terminal portions of said front wall on either side of said central portion;

a plurality of seats formed individually into said base within said recesses and each receptive of the base portion of a tubular jet tip;

a plurality of said jet tips;

an inlet defined in said top wall;

a cover shaped to envelope said cabinet and enclose said recesses, said dial and said inlet, said cover being invertible to serve as a reservoir and having in a horizontal wall a valve operable to release water into said inlet when said cover is inverted and mounted atop said top wall;

a pump disposed within said cabinet and responsive to said pressure control for delivering water from said inlet;

an elongated handle in one end of which is secured one of said jet tips and from the other end of which emerges a flexible hose receptive of water from said pump;

a hollow boss upstanding from a portion of said base and disposed to one side of said cabinet, the interior of said boss being sized to accept said other end of said handle;

and a cylindrical wall upstanding from said portion of said base and spaced around said boss by an amount sufficient to accommodate coiling of said hose as said other end of said handle is seated in said boss.

7. An oral hygiene appliance comprising:

a horizontally elongated base;

a cabinet upstanding from said base and having top, front and rear vertical walls;

a pressure control in said cabinet;

a pressure-control dial exposed on a laterally central portion of said front wall;

a pair of recesses individually formed in respective opposite terminal portions of said front wall on either side of said central portion;

a plurality of seats formed individually into said base within said recesses and each receptive of the base portion of a tubular jet tip;

a plurality of said jet tips;

an inlet defined in said top wall;

a cover shaped to envelope said cabinet and enclose said recesses, said dial and said inlet, said cover being invertible to serve as a reservoir and having in a horizontal wall a valve operable to release water into said inlet when said cover is inverted and mounted atop said top wall;

a pump disposed within said cabinet and responsive to said pressure control for delivering water from said inlet;

a handle receptive of one of said jet tips to enable delivery of said water to a point of use;

each of said jet tips having an elongated hollow shank terminating in its end portion opposite its output end with a circumferentially-faceted portion beyond which is defined a neck further beyond which is a nipple;

an elongated hollow housing;

a retaining collar secured within an upper end of said housing and having a plurality of circumferentially-spaced fingers disposed to project into engagement with said neck;

a cap embracing said collar and having a cross wall in which are defined a matching set of facets;

a conduit coupled to and extending beyond said nipple;

a valve operator accessible on said housing and operable to close said conduit;

another nipple secured to the end of said conduit beyond said operator;

and a flexible base coupled between said other nipple and said pump.

8. An oral hygiene appliance comprising:

an elongated generally tubular housing;

a battery, a motor energized by said battery and a motion translator driven by said motor all disposed within said housing with said translator having a fitting exposed through one end of said housing;

a generally horizontal base in which is defined a well of a size to receive and seat a terminal portion of said housing including the other end thereof;

a pedestal disposed atop said base to the rear of said well;

a plurality of mountings individually located in respective different positions on top of said pedestal;

another plurality of mountings individually located in respective different positions on top of said base alongside said well and in front of said pedestal;

and a plurality of brushes each having a shank with bristles distributed over one end portion thereof and with the other end portion defining a coupling selectively engageable with different ones of said fitting and said mountings.

9. An oral hygiene appliance as defined in claim 8 in which a charging coil is disposed in said base around said well.

10. An oral hygiene appliance comprising:
a horizontally-elongated base;
a cabinet upstanding from a portion of said base and enclosing an oral irrigation pump unit;
an elongated handle in one end of which is secured a jet tip to enable delivery to a point of use and from the other end of which emerges a flexible hose receptive of water from said pump unit;
a hollow boss upstanding from a portion of said base and disposed to one side of said cabinet, the interior of said boss being sized to accept said other end of said handle;
and a cylindrical wall upstanding from said portion of said base and spaced around said boss by an amount sufficient to accommodate coiling of said hose as said other end of said handle is seated in said boss.

11. An oral hygiene appliance as defined in claim 10 in which said other end includes a longitudinal slot defined in its exterior and in which a rib projects laterally from the interior wall of said boss for captivation of said slot.

12. An oral hygiene appliance as defined in claim 10 in which a relief is defined in the upper end surface of said boss and into which a portion of said hose rests as said handle seats in said boss.

13. An oral hygiene appliance delivery system comprising:
a jet tip with an elongated hollow shank terminating in an end portion opposite an output end with a circumferentially-faceted portion beyond which is defined a neck further beyond which is a nipple;
an elongated hollow housing;
a retaining collar secured within the upper end of said housing and having a plurality of circumferentially-spaced fingers projecting into engagement with said neck;
a cap embracing said collar and having a cross wall in which are defined a matching set of facets;
a conduit coupled to and extending beyond said nipple;
a valve operator accessible on said housing and operable to close said conduit;
another nipple secured to the end of said conduit beyond said operator;
and a flexible hose coupled between said other nipple and a source of irrigation.

14. An oral hygiene appliance having a pump housing into which water is supplied and from which said water is delivered through a flexible hose to a point of use and comprising:
a funnel-shaped pumping chamber defined in said housing to have a mouth joined by a side wall to a neck;
a flexible diaphram sealingly disposed across said mouth;
a rod at one end secured centrally to said diaphram and at the other end driven in reciprocation;
an outlet from said housing;
a passage between said neck and said outlet;
a first check valve in said passage to permit water flow only toward said outlet;
an inlet into said housing;
a duct between said inlet and an opening through said sidewall into said chamber;
a second check valve in said duct to permit water flow only toward said chamber;
an outwardly-facing well defined in said housing;
a bore formed in the bottom of said well;
an opening in said bottom of said well alongside said bore;
a passageway from said opening and into the sidewall of said pumping chamber;
a piston disposed in said bore;
a port through said housing from the head on one end of said piston into said passage at a location toward said outlet from the seat of said first check valve;
a radius-variable rotatable and axially movable cam defined on the other end of said piston and seatable within said well with said cam having a lateral flat normally covering said opening;
a spring urging said cam flat closed against said opening but enabling pressure beyond a limit in said passage to move said piston and bleed pressure through said passageway;
a portal formed in the sidewall of said well in alignment with said cam;
a pathway defined in said housing and leading from said portal to said inlet;
and a control knob coupling rotation to said cam in variation of the amount of pressure bled back from said chamber through said pathway to said inlet.

15. An oral hygiene appliance having a pump housing into which water is supplied and from which said water is delivered through a flexible hose to a point of use and comprising:
a pump in said housing and having a pumping chamber through which water is suctioned from an input and pressured into an output;
an outlet from said housing;
a passage between said output and said outlet;
an inlet into said housing;
a duct between said inlet and said output;
an outwardly-facing well defined in said housing;
a bore formed in the bottom of said well;
an opening in said bottom of said well alongside said bore;
a passageway from said opening and into said pumping chamber;
a piston disposed in said bore;
a port through said housing from the head on one end of said piston into said passage;
a radius-variable rotatable and axially movable cam defined on the other end of said piston and seatable within said well with said cam having a lateral flat normally covering said opening;

a spring urging said cam flat closed against said opening but enabling pressure beyond limit in said passage to move said piston and bleed pressure through said passageway;

a portal formed in the sidewall of said well in alignment with said cam;

a pathway defined in said housing and leading from said portal to said inlet;

and a control knob coupling rotation to said cam in variation of the amount of pressure bled back from said chamber through said pathway to said inlet.

16. An oral hygiene appliance as defined in claim 15 in which said well further includes a cup-shaped collar having said portal defined in the side wall thereof and including in the bottom wall thereof holes corresponding to said bore and said opening together with an elastomeric disc secured on the outer side of said bottom wall and having cylindrical pores individually seated at respective ones of said holes in ultimate delineation of said bore and said opening.

17. An oral hygiene appliance as defined in claim 16 in which said disc includes an integral lip aligned with said bore and sealingly receptive of said piston.

18. An oral hygiene appliance as defined in claim 16 in which said disc includes a hollow button aligned with and protruding through said opening to define a seal engageable against said land.

19. An oral hygiene appliance having a pump housing into which water is supplied and from which said water is delivered through a flexible hose to a point of use and comprising:

a pump in said housing and having a pumping chamber through which water is suctioned from an input and pressured into an output;

an outlet from said housing;

a passage between said output and said outlet;

an inlet into said housing;

a duct between said inlet and said output;

an outwardly-facing well defined in said housing;

a bore formed in the bottom of said well;

an opening in said bottom of said well alongside said bore;

a passageway from said opening and into said pumping chamber;

a piston disposed in said bore;

a port through said housing from the head on one end of said piston into said passage;

a radius-variable rotatable and axially movable cam defined on the other end of said piston and seatable within said well with said cam having a lateral flat normally covering said opening;

a spring urging said cam flat closed against said opening but enabling pressure beyond a limit in said passage to move said piston and bleed pressure through said passageway;

a portal formed in the sidewall of said well in alignment with said cam;

a pathway defined in said housing and leading from said portal to said inlet;

a control knob coupling rotation to said cam in variation of the amount of pressure bled back from said chamber through said pathway to said inlet;

a horizontally-elongated base;

a cabinet upstanding from a portion of said base and enclosing said pump housing;

an elongated handle in one end of which is secured a jet tip to enable delivery to a point of use and from the other end of which emerges a flexible hose receptive of water from said outlet;

a hollow boss upstanding from a portion of said base and disposed to one side of said cabinet, the interior of said boss being sized to accept said other end of said handle;

and a cylindrical wall upstanding from said portion of said base and spaced around said boss by an amount sufficient to accommodate coiling of said hose as said other end of said handle is seated in said boss.

20. An oral hygiene appliance having a pump housing into which water is supplied and from which said water is delivered through a flexible hose to a point of use and comprising:

a pump in said housing and having a pumping chamber through which water is suctioned from an input and pressured into an output;

an outlet from said housing;

a passage between said output and said outlet;

an inlet into said housing;

a duct between said inlet and said input;

an outwardly-facing well defined in said housing;

a bore formed in the bottom of said well;

an opening in said bottom of said well alongside said bore;

a passageway from said opening and into said pumping chamber;

a piston disposed in said bore;

a port through said housing from the head on one end of said piston into said passage;

a radius-variable rotatable and axially movable cam defined on the other end of said piston and seatable within said well with said cam having a lateral flat normally covering said opening;

a spring urging said cam flat closed against said opening but enabling pressure beyond a limit in said passage to move said piston and bleed pressure through said passageway;

a portal formed in the sidewall of said well in alignment with said cam;

a pathway defined in said housing and leading from said portal to said inlet;

a control knob coupling rotation to said cam in variation of the amount of pressure bled back from said chamber through said pathway to said inlet;

a jet tip with an elongated hollow shank terminating in its end portion opposite its output end with a circumferentially-faceted portion beyond which is defined a neck further beyond which is a nipple;

an elongated hollow housing;

a retaining collar secured within the upper end of said housing and having a plurality of circumferentially-spaced fingers projecting into engagement with said neck;

a cap embracing said collar and having a cross wall in which are defined a matching set of facets;

a conduit coupled to and extending beyond said nipple;

a valve operator accessible on said housing and operable to close said conduit;

another nipple secured to the end of said conduit beyond said operator;

and a flexible hose coupled between said other nipple and said outlet.

21. An oral hygiene appliance having a pump housing into which water is supplied and from which said water is delivered through a flexible hose to a point of use and comprising:

a funnel-shaped pumping chamber defined in said housing to have a mouth joined by a side wall to a neck;

a flexible diaphram sealingly disposed across said mouth;

a rod at one end secured centrally to said diaphram and at the other end driven in reciprocation;

an outlet from said housing;

a passage between said neck and said outlet;

a first check valve in said passage to permit water flow only toward said outlet;

an inlet into said housing;

a duct between said inlet and an opening through said side wall into said chamber;

a second check valve in said duct to permit water flow only toward said chamber;

and a control operable to bleed pressure from said chamber to said inlet in variation of pressure at said outlet.

* * * * *